(12) United States Patent
Graβl

(10) Patent No.: US 11,384,813 B2
(45) Date of Patent: Jul. 12, 2022

(54) CLAMPING DEVICE AND SENSOR CABLE

(71) Applicant: Drägerwerk AG & Co. KGaA, Lübeck (DE)

(72) Inventor: Thomas Graβl, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 167 days.

(21) Appl. No.: 17/032,688

(22) Filed: Sep. 25, 2020

(65) Prior Publication Data
US 2021/0095740 A1  Apr. 1, 2021

(30) Foreign Application Priority Data
Sep. 27, 2019 (DE) .................. 102019006783.5

(51) Int. Cl.
*F16G 11/04* (2006.01)
*A61B 5/282* (2021.01)

(52) U.S. Cl.
CPC ............ *F16G 11/044* (2013.01); *A61B 5/282* (2021.01)

(58) Field of Classification Search
CPC ....... F16G 11/044; A61B 5/282; A61B 5/274; Y10S 439/909; H01R 11/22; H01R 13/6335; H01R 2201/12; Y10T 24/44769; Y10T 24/44872
See application file for complete search history.

(56) References Cited

U.S. PATENT DOCUMENTS

| | | | |
|---|---|---|---|
| 3,616,497 A * | 11/1971 | Esposito, Jr. | A44B 99/00 606/205 |
| 4,040,697 A | 8/1977 | Ramsay et al. | |
| 4,854,323 A * | 8/1989 | Rubin | A61B 5/282 600/382 |
| 6,397,439 B1 | 6/2002 | Langford | |
| 6,487,430 B1 | 11/2002 | Henderson et al. | |
| 9,226,680 B1 | 1/2016 | Kendricks | |

(Continued)

FOREIGN PATENT DOCUMENTS

| | | |
|---|---|---|
| DE | 40 09 938 A1 | 10/1991 |
| DE | 19618611 A1 | 9/1997 |

(Continued)

OTHER PUBLICATIONS

Product Information: MonoLead® ECG Lead-Wire Set (Year: 2015).*

*Primary Examiner* — Robert Sandy
*Assistant Examiner* — Rowland Do
(74) *Attorney, Agent, or Firm* — McGlew and Tuttle, P.C.

(57) ABSTRACT

A clamping device (1), for coupling a sensor cable (2) to an electrical contact, has a circumferential, elastically deformable frame (3). The frame has an outer surface (5), an inner surface (6) facing an inner area (4), a first end face (7) and an opposite second end face (8). A contact device (9) is held at the frame and extends into the inner area. A counter-holding device (10), at the frame, has a counter-holding element (11). The contact device and the counter-holding device form a receiving space for holding the electrical contact in a holding position. A relative movement into a first released position is brought about by a pressing on both sides from the outside against the outer surface on a first frame axis (12). A second released position is provided by pressing on both sides against the frame outer surface on a second frame axis (13).

20 Claims, 7 Drawing Sheets

(56) References Cited

U.S. PATENT DOCUMENTS

| | | |
|---|---|---|
| 9,728,871 B1 | 8/2017 | Gutgold et al. |
| 2002/0019166 A1 | 2/2002 | Ubby et al. |
| 2004/0203273 A1 | 10/2004 | Schwarz |
| 2005/0048640 A1* | 3/2005 | Kennedy ............ F16B 2/20 24/518 |
| 2011/0151728 A1 | 6/2011 | Astola |

FOREIGN PATENT DOCUMENTS

| | | |
|---|---|---|
| DE | 196 43 988 C1 | 4/1998 |
| GB | 171317 A | 11/1921 |
| JP | S39004538 B | 2/1964 |
| JP | S4815173 B | 6/1971 |
| JP | S56117478 B | 2/1981 |
| JP | H0447683 A | 2/1992 |
| WO | 03070097 A1 | 8/2003 |

\* cited by examiner

CLAMPING DEVICE AND SENSOR CABLE

CROSS REFERENCE TO RELATED APPLICATIONS

This application claims the benefit of priority under 35 U.S.C. § 119 of German Application 10 2019 006 783.5, filed Sep. 27, 2019, the entire contents of which are incorporated herein by reference.

TECHNICAL FIELD

The present invention pertains to a clamping device for electrically coupling a sensor cable to an electrode. The present invention further pertains to a sensor cable for electrically coupling an electrode to a diagnostic device.

TECHNICAL BACKGROUND

It is known that sensor cables can be coupled electrically to an electrode via a clamping device. Conventional electrodes often have to this end an electrically conductive rivet, to which the clamping device can be clamped. Another end of the sensor cable is configured for the electrical coupling to a diagnostic device, for example, to a patient monitor, to an electrocardiogram (ECG and also known as EKG) apparatus, to an electroencephalogram (EEG) apparatus or the like and it has for this purpose, for example, a multipolar plug. For example, a potential difference between two electrodes can be detected by means of the diagnostic device and be outputted in a visualizable manner and/or acoustically for a person operating the diagnostic device. Diagnostic devices may be configured, for example, to determine as well as optically and/or acoustically to output a heart rate or an ST segment from such a potential difference as a function of the time and the change in the potential difference.

Various clamping devices of this class are known from the documents U.S. Pat. No. 9,226,680 B, DE 196 43 988 C1, U.S. Pat. Nos. 4,040,697 A, 6,397,439 B, DE 40 09 938 A1, US 2011 151 728 A and US 2004 203 273 A. These clamping devices have a clamping area with two clamping jaws and an actuating area with two actuating surfaces. By applying a pressing force to the actuating surfaces, the clamping jaws of the clamping areas can be moved away from one another, so that the clamping device can be placed at the electrode and can be separated from the electrode. By reducing the pressing force acting on the actuating surfaces, the clamping devices can be moved again towards one another. The clamping devices have a resetting spring or a resetting spring section for this purpose.

Conventional clamping devices for electrically coupling a sensor cable to an electrode have especially the drawback that unfavorable forces and torques can be transmitted to the electrode and hence to the patient due to a twisting of the sensor cable. In addition, conventional clamping devices often have only one preferred side, via which they can be coupled to the electrode. Another drawback of many clamping devices is that the actuating surfaces are accessible to an operating person only with difficulty in case of electrodes arranged comparatively close to one another, so that an unintended overturning torque is often transmitted to the electrode especially during the separation of the clamping device from the electrode. This problem occurs especially in case of small patients, for example, infants. Moreover, many clamping devices have the drawback that they have partition lines, which can only be disinfected in a highly complicated manner. Finally, most clamping devices are unsuitable or only conditionally suitable for use in case of so-called "monoleads," i.e., when a plurality of cables are combined into an overall cable, due to the geometric configuration.

SUMMARY

Based on this state of the art, a basic object of the present invention is to provide a clamping device as well as a sensor cable, which do not have these drawbacks or are at least partially free from these drawbacks. Therefore, the object of the present invention is, in particular, to provide a clamping device for electrically coupling a sensor cable to an electrode as well as a sensor cable for electrically coupling an electrode to a diagnostic device, which ensure a simple electrical coupling as well as uncoupling of the clamping device and of the electrode with simple means as well as in a cost-effective manner and guarantee in the process improved handling for the operating person and/or improved comfort for the patient.

The above object is accomplished by a clamping device having features according to the invention. Features and details that are described in connection with the clamping device according to the present invention are, of course, also valid in connection with the sensor cable according to the present invention and vice versa, so that reference is and can always mutually be made to the individual aspects of the present invention concerning the disclosure.

According to a first aspect of the present invention, the object is accomplished by a clamping device for electrically coupling a sensor cable to an electrical contact. The clamping device has a circumferential, elastically deformable frame, said frame having a frame inner area, a frame outer surface facing away from the frame inner area, a first frame end face and a second frame end face located opposite the first frame end face. The clamping device further has a contact device held at the frame as well as extending into the frame inner area for being in contact with the electrical contact as well as a counter-holding device arranged at the frame with a counter-holding element. The contact device and the counter-holding device are configured to form in a holding position of the clamping device a receiving space for receiving as well as for holding the electrical contact. The clamping device is configured according to the present invention such that by applying pressure on both sides against the frame outer surface on a first frame axis passing through the frame inner area, a relative movement of the counter-holding device in relation to the contact device into a first released position can be brought about for releasing the electrical contact from the receiving space. In addition, the clamping device is configured such that by a pressure on both sides from the outside against the frame outer surface on a second frame axis passing through the frame inner area, which said axis is different from the first frame axis, a relative movement of the counter-holding device in relation to the contact device can be brought about into a second released position different from the first released position for releasing the electrical contact from the receiving space.

The clamping device is preferably configured to form the holding position in a relaxed state. Further, the clamping device is configured for electrical as well as mechanical coupling to a rivet of the electrical contact. The electrical contact may be configured, for example, as an electrical contact of an electrode, for example, an electrode that is normally used for ECG measurements in persons. The receiving space formed in the frame inner area of the contact device and of the counter-holding device is configured to receive the rivet at least partially. The receiving space is formed, for example, by the contact device and by the counter-holding device such that the rivet is held in a positive-locking manner in the receiving space in the holding position. Three mutually spaced-apart holding points, which are provided by the contact device and by the counter-holding device, are sufficient for this. The clamping device is preferably also configured to enclose the rivet over the entire circumference thereof or at least over a part of the circumference thereof. Enclosure over the entire circumference is defined within the framework of the present invention as an enclosure over at least 360°.

The clamping device especially preferably has no narrow joints, especially between parts of the clamping device that are movable relative to one another. A narrow joint is, for example, a joint between two directly adjacent parts or between two parts that touch one another. A joint with a joint width greater than 2 mm is, at any rate, not a narrow joint within the framework of the present invention. This has the advantage that the clamping device can be cleaned and disinfected especially easily. The risk of infection for patients is thus reduced.

The first frame axis preferably intersects a frame central axis, which passes through a surface center of the first frame end face and a surface center of the second frame end face. Points of application of forces for elastically compressing the frame are thus located in opposite locations on the frame outer surface. The first frame axis preferably intersects the frame central axis in a center between the first frame end face and the second frame end face. The first frame axis preferably extends parallel to the first frame end face and/or to the second frame end face. The second frame axis preferably intersects the frame central axis. The second frame axis preferably intersects the frame central axis in the center between the first frame end face and the second frame end face. The second frame axis preferably extends parallel to the first frame end face and/or to the second frame end face. The first frame axis and the second frame axis are preferably located on a common plane. It is preferred according to the present invention that an angle between the first frame axis and the second frame axis is between 45° and 90°. This angle preferably equals 90°.

The frame has an elastically deformable configuration. This means that due to a deformation of the frame by pressing forces acting on the frame outer surface, a resetting force of the frame can be brought about, the resetting force being configured to restore the frame into the original shape. The clamping device is configured for holding the electrical contact or a rivet of the electrical contact in the holding position, especially when the frame is relaxed. Provisions may be made according to the present invention for a filler, for example, a foam, a mesh structure or the like, to be arranged in a partial area of the frame inner area. The stability of the clamping device can be improved hereby.

To hold the electrical contact or the rivet of the electrical contact, the clamping device has the contact device as well as the counter-holding device, which extend into the frame inner area. According to the present invention, the counter-holding device has a counter-holding element, which is movable, preferably pivotable in relation to the contact device. In the relaxed state, the rivet can be held or clamped between the contact device and the counter-holding element in the receiving space. A relaxed state is defined within the framework of the present invention especially as a state of the frame in which no pressing force acts on both sides against the frame outer side. However, the frame may have an elastic stress in the relaxed state, for example, when an object, especially a rivet of an electrical contact, is arranged and is thus in contact with the contact device and with the counter-holding device. The contact device and/or the counter-holding element are preferably configured to mesh with an undercut of the rivet in the relaxed state of the frame.

Also, no additional holding elements are preferably provided in order to improve a deformation of the clamping device into the first released position as well as into the second released position for separating the rivet from the clamping device. The first released position and the second released position of the clamping device are defined within the framework of the present invention such that the contact device and the counter-holding device, especially the counter-holding element, are arranged in relation to one another such that the receiving space is open in at least one direction for the rivet to move out of the receiving space. The rivet can thus easily be separated from and inserted into the clamping device in the first released position as well as in the second released position of the clamping device.

There are two possibilities according to the present invention for separating a rivet from the clamping device and for the electrical as well as mechanical coupling of the clamping device to the rivet. The frame can be deformed by pressing on both sides onto the frame outer surface on the first frame axis such that the contact device and the counter-holding device assume the first released position relative to one another. In the first released position, the receiving space is open for releasing the rivet in at least one direction, so that the rivet can be separated from the clamping device. By pressing on both sides of the frame outer surface on the second frame axis, the frame can be deformed such that the contact device and the counter-holding device assume relative to one another the second released position, the second released position being different from the first released position.

A clamping device according to the present invention has the advantage over conventional clamping devices that an electrical as well as mechanical coupling to an electrical contact, especially to a rivet of an electrical contact, for example, of a commercially available ECG electrode for adults or children, is guaranteed with simple means as well as in a cost-effective manner. In addition, the clamping device has the great advantage that opening of the clamping device can be brought about by pressing on both sides of the frame outer surface on different frame axes of the clamping device. This is especially advantageous in case of electrical contacts, especially electrodes, which are located close to one another, when a working point for opening the clamping device is located so close to an adjacent clamping device that opening of the clamping device is hindered by the adjacent clamping device. An unintended collision with other clamping devices can thus easily be avoided by the frame being compressed for opening on both sides on a second frame axis rotated by 90° in relation to the first frame axis.

According to a preferred variant of the present invention, provisions may be made in a clamping device for the clamping device to be configured such that the counter-holding device can be caused to move away from the contact device by pressing on both sides of the frame outer surface on the first frame axis. It is preferred to this end that the counter-holding device extends along the second frame axis. The frame can preferably be deformed by pressing on both sides against the frame such that the pressure points move closer to one another and frame points spaced by about 90° from the pressure points move away from one another. The counter-holding device is preferably arranged at the frame adjacent to one of these frame points, so that the distance between the counter-holding device and the contact device is thus increased. This has the advantage that the first released position is obtained with simple means as well as in a cost-effective manner.

The clamping device is preferably configured such that the counter-holding element can be caused to move away from the second frame axis by pressing on both sides against the frame outer surface from the outside on the second frame axis. The frame can preferably be deformed by pressing on both sides against the frame such that the pressure points move closer to one another and frame points spaced by about 90° from the pressure points move away from one another. The counter-holding device is preferably arranged at the frame adjacent to one of these frame points, so that a pivoting away of the counter-holding device or of the counter-holding element can be brought about hereby, especially in interaction with a rivet arranged in the receiving space. This has the advantage that the second releasing position is obtained with simple means as well as in a cost-effective manner.

It is preferred that the counter-holding device has two counter-holding elements, the clamping device being configured such that the counter-holding elements can be caused to move away from one another by pressing on both sides against the frame outer surface on the second frame axis. The frame can thus be deformed by pressing on both sides on the frame outer surface on the second frame axis such that a distance between the two counter-holding elements from one another is increased, especially by pivoting the counter-holding elements mutually away from one another. The second released position is obtained hereby. The clamping device is preferably configured such that the two counter-holding elements move away from one another in opposite directions. Provisions may be made in this connection according to the present invention for the counter-holding elements to perform different movements in terms of direction and/or extent. As an alternative, the clamping device may be configured such that only one counter-holding element moves, especially pivots, away from the other counter-holding element during such an actuation, and the other counter-holding element does not change its relative position relative to the contact device. Additional counter-holding elements may be provided according to the present invention as well. Further, the clamping device is preferably configured such that the counter-holding elements can be moved away from one another, preferably pivoted away from one another, by pressing on both sides of the frame outer surface of a frame axis, which is rotated by up to about 30° in relation to the second frame axis. Two or more counter-holding elements have the advantage that a holding force of the clamping device can be increased as well as separation of the clamping device can be facilitated with simple means as well as in a cost-effective manner.

According to a preferred variant of the present invention, provisions may be made in a clamping device for the frame to have a plurality of hinge areas, wherein said hinge areas are configured to yield in response to the pressing on both sides against the frame outer surface on the first frame axis and/or on the second frame axis. It is preferred in this connection that at least two hinge areas are arranged at equal distances to the adjacent first frame axis or to the second frame axis. The hinge areas are configured each as a tapered section of the frame. The tapered section preferably pertains to a distance between the frame outer surface and the frame inner surface. In addition or as an alternative, the hinge areas may also be formed from another material, especially from a material with an elasticity higher than that of the frame areas formed between the hinge areas. The frame areas formed between the hinge areas may also have a non-elastic or rigid configuration according to the present invention. The elastic deformability according to the present invention of the frame is preferably ensured in this case by means of the hinge areas. Hinge areas have the advantage that a more rigid frame material can be used and that a deformation of the frame for opening the clamping device by pressing on both sides of the frame outer side is facilitated with simple means as well as in a cost-effective manner.

It is preferred according to the present invention that at a contact end facing the counter-holding device, the contact device has a contact recess for the partially enclosing contact of the electrical contact. The contact recess preferably has an arch with an inner radius, which corresponds or at least essentially corresponds to an outer radius of a rivet of a commercially available electrical contact, especially of a commercially available electrode, for example, of an ECG electrode for an adult or for a child. Such a contact recess has especially the advantage that an especially reliable holding of the clamping device at the electrical contact is guaranteed with simple means as well as in a cost-effective manner.

Further, an electrical contact for electrically coupling the clamping device to the electrical contact is preferably arranged at the contact device. As an alternative or in addition, an electrical contact may also be arranged at the counter-holding device, especially at the first counter-holding element and/or at a second counter-holding element, which may possibly be present. The electrical contact is preferably arranged at the contact end. Further, the electrical contact preferably forms the contact end or at least a part of the contact end. The electrical contact preferably has a contact thickness that corresponds at least to half the frame thickness of the frame. The thickness of the frame is defined within the framework of the present invention as the distance between the frame outer surface and the frame inner surface. The electrical contact preferably has a contact thickness that corresponds at least to half of the contact thickness of the contact device. The electrical contact is preferably configured and arranged such that when the frame is relaxed and the electrical contact is held at the clamping device, an electrical contact is established between the rivet of the electrical contact and the electrical contact. This has the advantage that an electrical contact can be established between a sensor cable and the electrical contact with simple means as well as in a cost-effective manner.

Provisions may be made in a clamping device in an especially preferred embodiment of the present invention for the electrical contact to be configured and arranged such that an electrical coupling of the clamping device to an electrical contact can be brought about both via the first frame end face and the second frame end face of the clamping device. It is preferred here if the electrical contact has a symmetrical configuration. This has the advantage that coupling of the clamping device to the electrical contact is simplified with simple means as well as in a cost-effective manner, because the coupling can be brought about via any desired frame end face of the clamping device. An orientation of the clamping device to the electrical contact is accordingly simplified correspondingly, so that the coupling may also be carried out, for example, blindly by the operating person.

The frame outer surface preferably has at least partially a slip-blocking surface. The slip-blocking surface is preferably formed at least in an intersection area of the first frame axis and/or the second frame axis with the frame outer surface. A slip-blocking surface segment preferably has a segment length of at least 1 cm in the circumferential direction of the frame. As an alternative, the slip-blocking surface may also be arranged over the entire circumference on the frame outer side. Further, the complete frame outer side is configured as a slip-blocking surface (anti-slip surface/grasping surface). The slip-blocking surface preferably has a roughed surface, ripples, nubs or the like. As an alternative or in addition, the slip-blocking surface may be configured as a coating or have a coating. The frame outer side preferably has a marking in the intersection area for visualizing preferred pressure points. The visualization may also be configured according to the present invention as a greater frame thickness of the frame. As an alternative or in addition, the visualization may be configured as a grey scale contrast and/or color contrast. This has the advantage that the operation of the clamping device, especially the deformation of the frame, by pressing on both sides is simplified with simple means as well as in a cost-effective manner, because the risk of slipping off from the pressure points is reduced and the preferred pressure points can be better recognized by the operating person.

According to a preferred embodiment of the present invention, at least one of the frame end faces has a planar and/or arched configuration. Both frame end faces preferably have a planar or arched configuration. The arch is preferably convex. Further, at least one edge, and preferably both edges are rounded between the frame end faces and the frame outer side. The surface of the clamping device, especially of the frame end faces, is essentially smooth. This has the advantage that a clamping device that can be cleaned and disinfected especially easily is provided with simple means as well as in a cost-effective manner.

The clamping device is preferably made in one piece from a plastic. The plastic preferably possesses springy properties. Such a clamping device can be manufactured with simple means as well in a cost-effective manner.

The clamping device especially preferably has a cable interface for electrically coupling the clamping device to a cable, the cable interface being configured for laterally guiding the cable in relation to the frame inner area. In other words, the cable interface is configured to guide the cable along a tangent or a secant near a tangent. This consequently means for a sensor cable that the clamping device laterally projects from the cable of the sensor cable. The cable interface is preferably configured for linearly guiding the cable. This has the advantage that it is possible to manufacture a sensor cable with simple means and in a cost-effective manner, which sensor cable makes it possible to couple the clamping device to an electrical contact and in which the coupling transmits especially low bending torques from the cable to the electrical contact.

Further, the clamping device preferably has a spring element extrusion-coated with a plastic. The spring element is preferably manufactured from a spring steel or the like. Such a clamping device can be manufactured with simple means as well as in a cost-effective manner and possesses, moreover, improved springy properties.

According to a second aspect of the present invention, the object is accomplished by a sensor cable for electrically coupling an electrical contact to a diagnostic device. The sensor cable has an at least unipolar cable and at least one clamping device for electrically coupling the sensor cable to the electrical contact. The at least one clamping device is configured according to the present invention as a clamping device according to the present invention.

The clamping device is preferably coupled mechanically to the cable such that the clamping device projects laterally from the cable and is held eccentrically at the cable. Moreover, the clamping device is preferably coupled electrically to the cable such that an electrical contact of the clamping device is coupled electrically to a conductor of the cable for the electrical coupling of the clamping device to an electrical contact, especially to a rivet of an electrical contact, especially to an electrode.

All the advantages that were already described in connection with the clamping device according to the first aspect of the present invention are present in the sensor cable described. Accordingly, the sensor cable according to the present invention has the advantage over conventional sensor cables that an electrical as well as mechanical coupling of the sensor cable to an electrical contact, especially to a rivet of an electrode, for example, of a commercially available ECG electrode for adults or children, is guaranteed with simple means as well as in a cost-effective manner. In addition, the sensor cable has the great advantage that opening of the clamping device can be brought about by pressing on both sides of the frame outer surface on different frame axes of the clamping device. This is especially advantageous in case of electrical contacts located close to one another when a point of application for opening the clamping device is located so close to an adjacent clamping device that the opening of the clamping device is hindered by the adjacent clamping device. An unintended collision with other clamping devices can thus easily be avoided by the frame being compressed on both sides for opening the frames, for example, on a second frame axis rotated by 90° in relation to the first frame axis.

A multipolar configuration of the cable with a plurality of conductors is preferred and the sensor cable preferably has a plurality of clamping devices, the clamping devices being coupled electrically each with a different conductor of the cable. The clamping devices are preferably coupled mechanically to the cable such that the clamping devices project laterally from the cable and are held eccentrically at the cable. Moreover, the clamping devices are preferably coupled electrically with a cable conductor of their own such that an electrical contact of the clamping device is coupled electrically to the respective conductor of the cable for the electrical coupling of the clamping device to an electrical contact, especially to a rivet of the electrode. This has the advantage that a plurality of electrical contacts can be coupled to the sensor cable with simple means as well as in a cost-effective manner.

The at least one clamping device is especially preferably connected, especially cast (molded on) integrally to the cable especially in a watertight and/or positive-locking manner. It is preferred in this connection if no partition lines are formed between the at least one clamping device and the cable. This has the advantage that a sensor cable that can be cleaned easily and disinfected easily is provided with simple means as well as in a cost-effective manner and the risk of infection is thus reduced for the patients.

Further measures improving the present invention appear from the following description of some exemplary embodiments of the present invention, which are shown in the figures. All the features and/or advantages appearing from the claims, from the description or from the drawings, including design details and arrangements in space, may be essential for the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
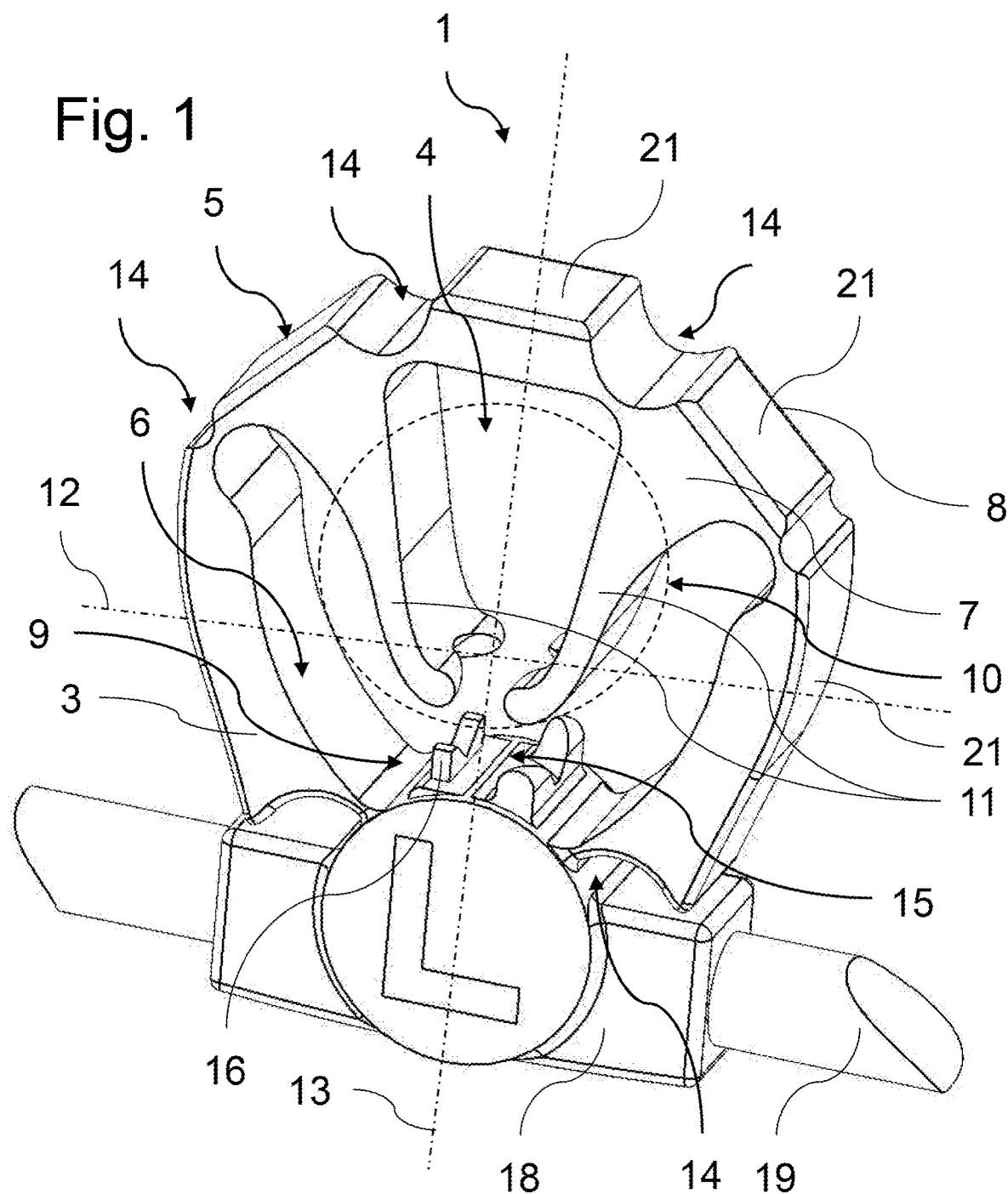
FIG. 1 is a perspective view of a preferred first embodiment of a clamping device according to the present invention.

Referring to the drawings, elements having the same function and mode of operation are always provided with the same reference numbers in FIGS. 1 through 7.

Figure 2:
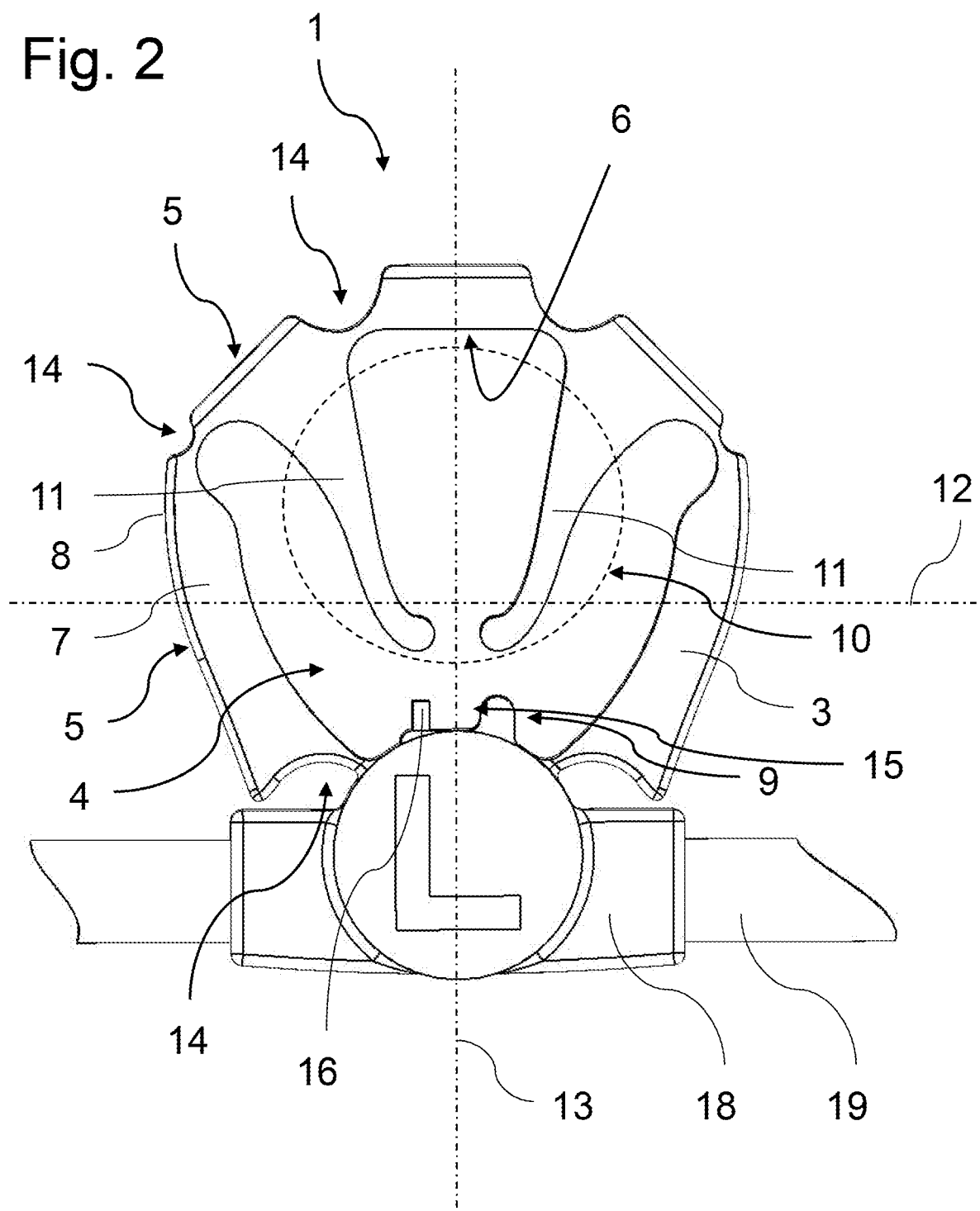
FIG. 2 is a top view of the clamping device from FIG. 1.

A preferred first variant of a clamping device 1 according to the present invention is shown schematically in a perspective view in FIG. 1 and FIG. 2. The clamping device 1 has a circumferential frame 3, which encloses a frame inner area 4 over the entire circumference thereof. The frame 3 has a frame outer surface 5 facing away from the frame inner area 4, a frame inner surface 6 facing the frame inner area 4 as well as a visible, first frame end face 7 formed between the frame outer surface 5 and the frame inner surface 6, and a second frame end face 8, which is not visible in this view and is located opposite the first frame end face 7.

The frame 3 has a plurality of hinge areas 14 distributed over the frame 3. The hinge areas 14 are configured in this preferred first exemplary embodiment as tapered sections of the frame 3 as well as a concave course of the frame outer surface 5. Areas of the frame outer surface 5, which are formed between the hinge areas 14, are configured as application surfaces 21 for an operating person for compressing on both sides of the frame 3. On one side of the frame 3, which is the lower side in these views, a cable interface 18 is formed in the frame 3. The clamping device 1 is coupled electrically and mechanically to a cable 19 via the cable interface 18. The cable interface 18 is configured such that the cable 19 is guided essentially tangentially to the frame 3.

On a side of the cable interface 18 facing the frame inner area 4, a contact device 9 is formed for contacting a rivet, not shown, of an electrical contact, not shown. The contact device 9 has a contact recess 15 for receiving a partial area of the rivet. An area of the contact recess 15 is configured as an electrical contact 16 for establishing an electrical coupling between the rivet and the cable 19. A counter-holding device 10 is arranged on a side of the frame 3, which side is located opposite the contact surface 9. The counter-holding device 10 has two counter-holding elements 11, which are located at spaced locations from one another and which extend, converging towards one another, into the frame inner area 4. End areas of the counter-holding elements 11, which end areas are adjacent to the contact device 9, are configured for being in contact with the rivet of the electrical contact. The clamping device 1 is shown in a relaxed state, i.e., in a holding state for holding the rivet of the electrical contact.

FIG. 1 and FIG. 2 show as examples a first frame axis 12 and a second frame axis 13 arranged at 90° in relation to the first frame axis 12. The first frame axis 12 and the second frame axis 13 span a common area, which is arranged parallel to the first frame end face 7 and to the second frame end face 8, respectively, as well as between the first frame end face 7 and the second frame end face 8. By pressing on both sides against the application surfaces 21 on the first frame axis 12, the frame parts of the frame 3, which are the left frame part and the right frame part in this view, can be moved towards one another. The consequence of this is that the frame parts of the frame, which are the upper frame part and the lower frame part in this view, move away from one another. The contact device 9 and the counter-holding device 10 are thus caused hereby to move away from one another, so that the rivet of the electrical contact can be released. The frame parts of the frame 3, which are the upper frame part and the lower frame part in this view, can be moved towards one another by pressing on both sides against the application surfaces 21 on the second axis 13. The consequence of this is that the two counter-holding elements 11 are pivoted away from one another, so that the rivet of the electrical contact can be released.

Figure 3:
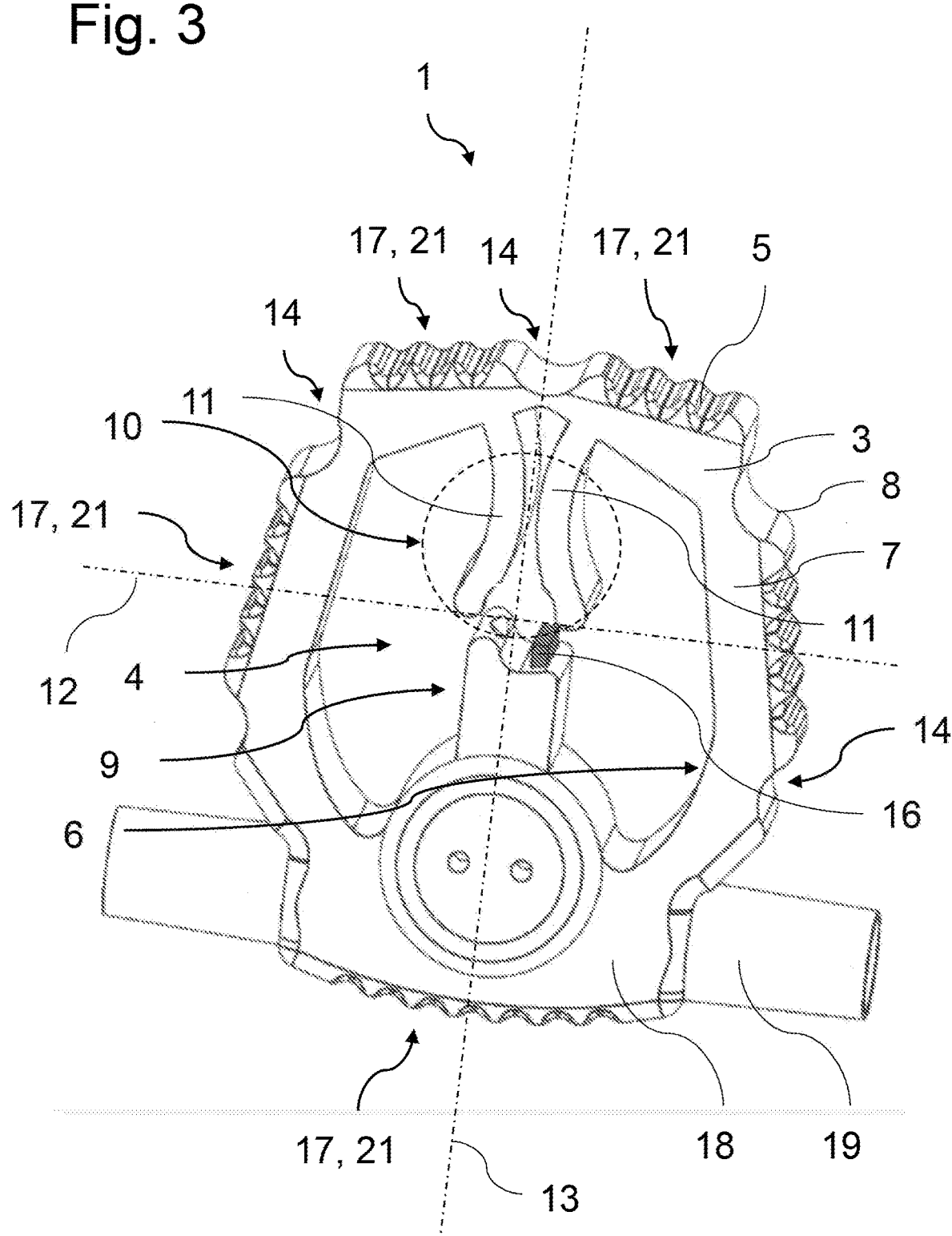
FIG. 3 is a perspective view of a preferred second embodiment of a clamping device according to the present invention.

A preferred second embodiment of a clamping device 1 according to the present invention is shown in FIG. 3 schematically in a perspective view. The clamping device 1 differs from the clamping device 1 according to the first embodiment especially in a connection of the counter-holding elements 11 to the frame 3. In addition, a hinge area 14 is arranged on the second frame axis 13. Finally, the application surfaces 21 of the frame outer surface 5 have a slip-blocking surface 17.

Figure 4:
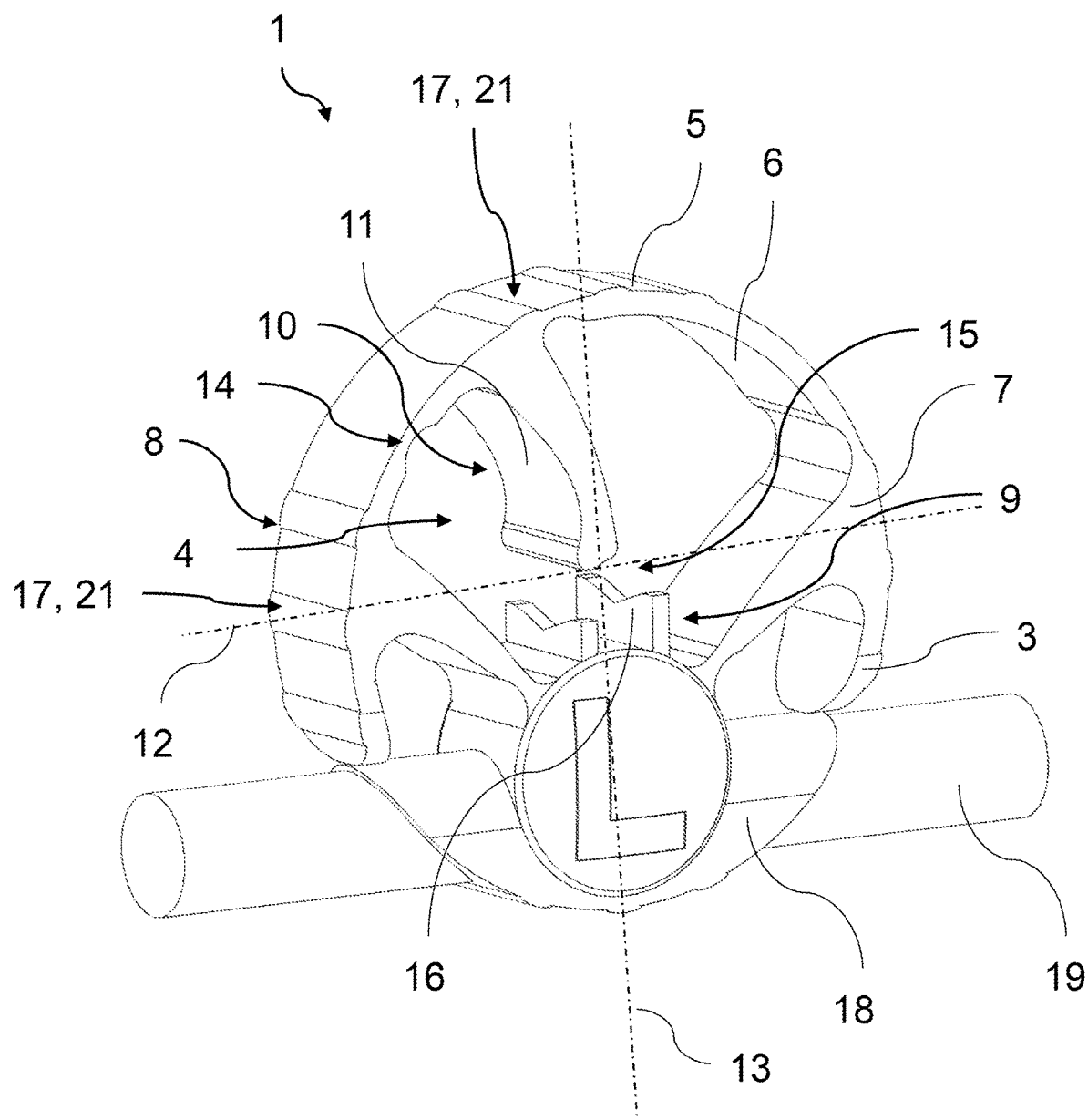
FIG. 4 is a perspective view of a preferred third embodiment of a clamping device according to the present invention.

FIG. 4 shows schematically a preferred third embodiment of a clamping device 1 according to the present invention in a perspective view. The clamping device 1 according to the third embodiment differs from the clamping devices 1 according to FIGS. 1 through 3 especially in that the counter-holding device 10 has only one counter-holding element 11. The counter-holding element 11—and hence the entire counter-holding device 10—is arranged obliquely in relation to the contact device 9. In an alternative embodiment, the counter-holding element 11 may also point directly towards the contact device 9 or be arranged with the contact device 9 in a common alignment. The frame 3 is relaxed in the state shown, so that a rivet of an electrical contact can be clamped in the clamping device 1. The frame parts of the frame 3, which are the upper frame part and the lower frame part in this view, can be moved towards one another by pressing on both sides against the application surfaces 21. The consequence of this is that the counter-holding element 11 is pivoted away from the contact device 9, clockwise in this view, so that the rivet of the electrical contact can be released.

Figure 5:
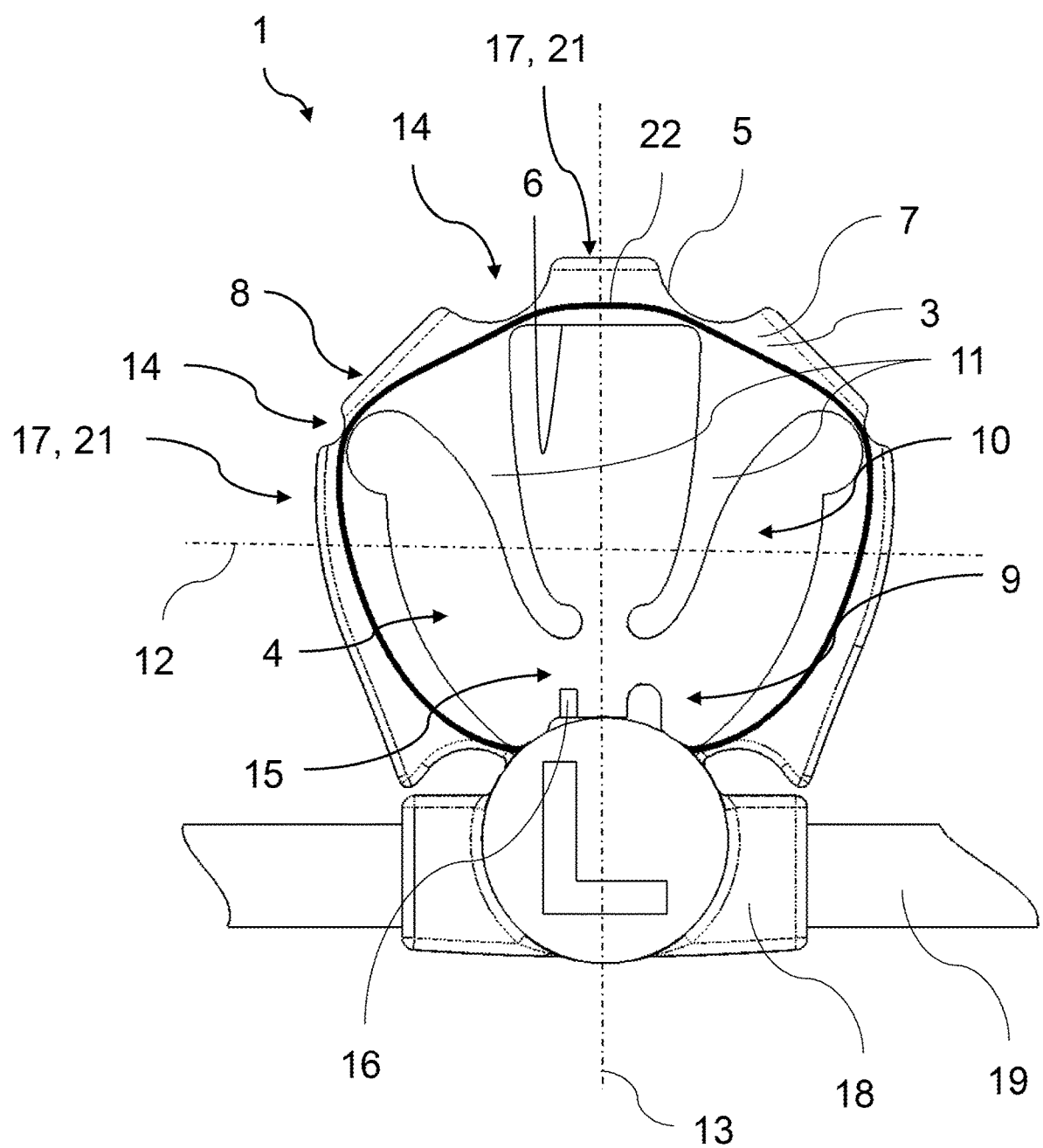
FIG. 5 is a side view of a preferred fourth embodiment of a clamping device according to the present invention.

FIG. 5 schematically shows a preferred fourth embodiment of a clamping device 1 according to the present invention in a top view. The clamping device 1 according to the fourth embodiment differs from the clamping devices 1 according to FIGS. 1 through 3 especially in that the frame has an approximately ring-shaped spring element 22, which is cast in or extrusion-coated. It is accordingly preferred that the spring element 22 is arranged between the frame outer surface 5, the frame inner surface 6, the first frame end face 7 and the second frame end face 8 of the frame 3. The spring element 22 is configured to reset the frame 3 into the relaxed state shown after a deformation, and a rivet can be clamped by the clamping device 1 in the relaxed state of the frame 3. The spring element 22 is interrupted in the area of the cable interface 18. The spring element 22 is preferably held at the cable interface 18 or is fixed at same. The spring element 22 preferably consists of spring steel or preferably has at least spring steel.

Figure 6:
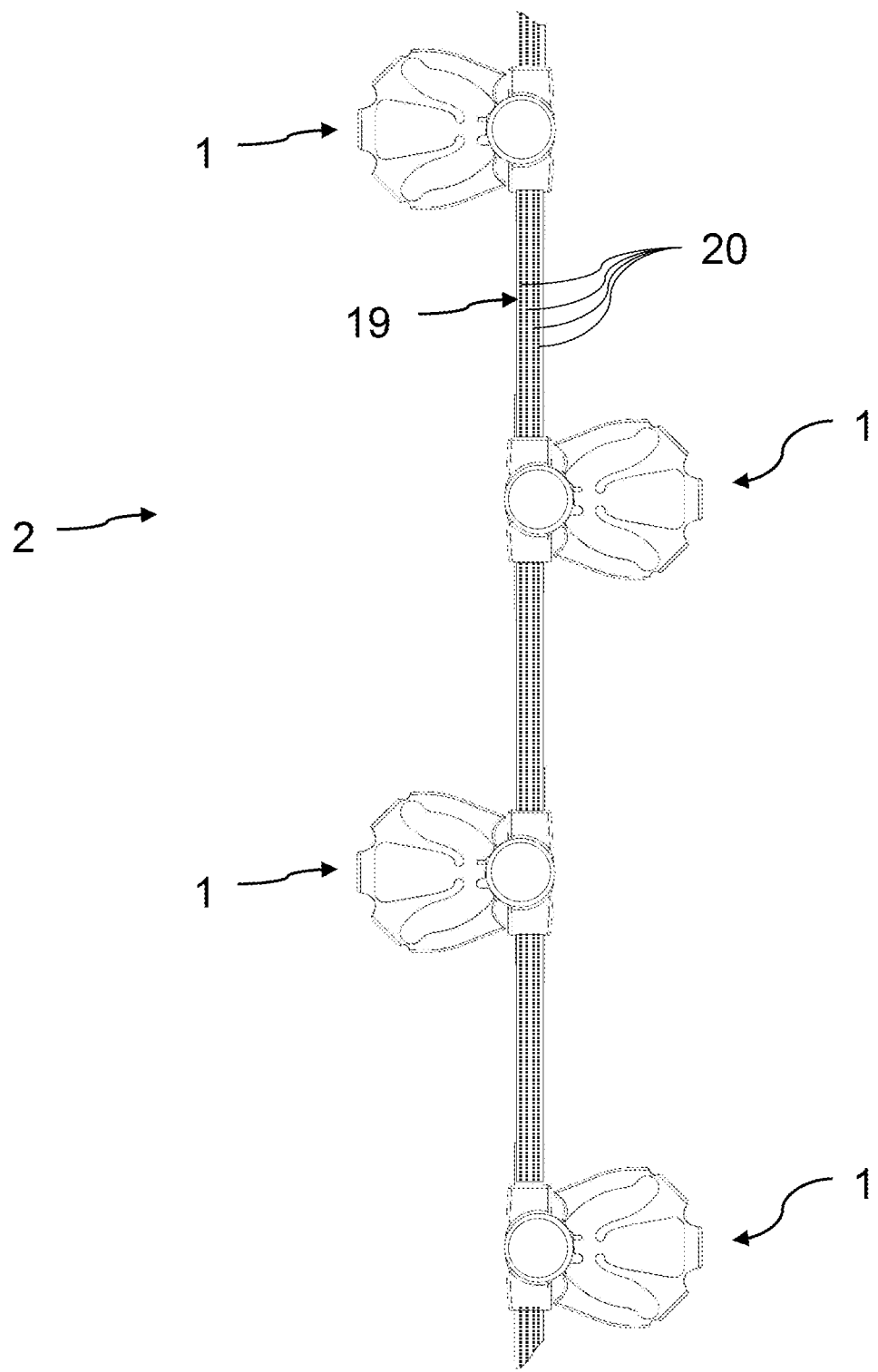
FIG. 6 is a top view of a preferred first embodiment of a sensor cable according to the present invention.

FIG. 6 shows schematically a preferred first embodiment of a sensor cable 2 according to the present invention in a top view. Only a detail of the sensor cable 2 is shown in this view. The sensor cable 2 preferably has a plug, not shown, at one end for electrical coupling to an analysis device. The sensor cable 2 has a cable 19 with a plurality of individual conductors 20 electrically insulated from one another. A plurality of clamping devices 1 according to the present invention are arranged at spaced locations from one another at the cable 19 such that these project laterally from the cable 19. The clamping devices 1 project from the cable 19 on two opposite sides in this exemplary embodiment. It is preferred that the clamping devices 1 are held at the cable 19 such that no partition lines are present between the clamping devices 1 and the cable 19. This has the advantage that the sensor cable 2 can thus be disinfected more easily. Each clamping device 1 is coupled electrically to another conductor 20 of the cable 19.

Figure 7:
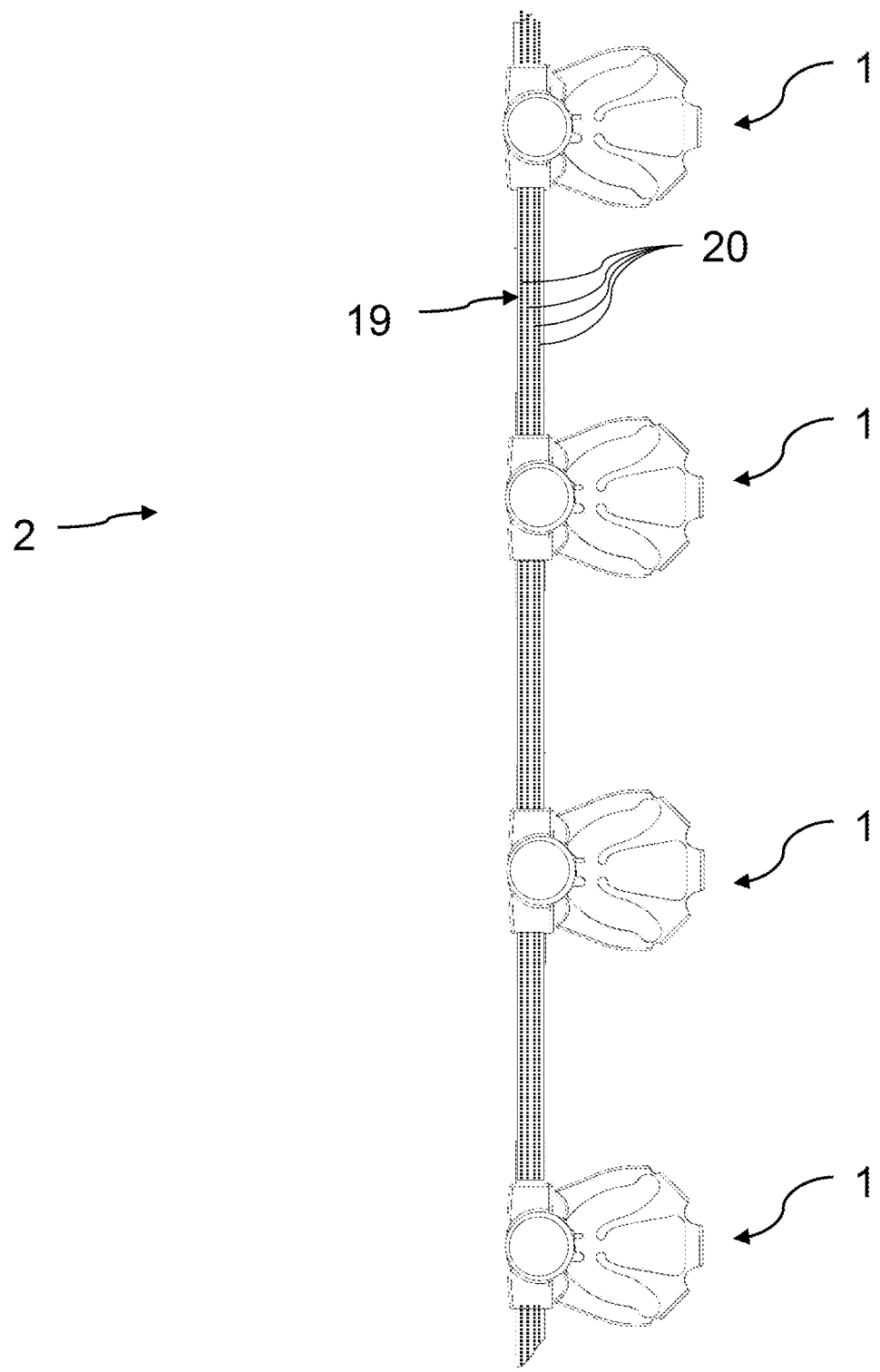
FIG. 7 is a top view of a preferred second embodiment of a sensor cable according to the present invention.

FIG. 7 schematically shows a preferred second embodiment of a sensor cable 2 according to the present invention in a top view. The preferred second embodiment of the sensor cable 2 according to the present invention differs from the first embodiment shown in FIG. 6 especially in the feature that all the clamping devices 1 project from the cable 19 on the same side.

While specific embodiments of the invention have been shown and described in detail to illustrate the application of the principles of the invention, it will be understood that the invention may be embodied otherwise without departing from such principles.

LIST OF REFERENCE NUMBERS

1 Clamping device
2 Sensor cable
3 Frame
4 Frame inner area
5 Frame outer surface
6 Frame inner surface
7 First frame end face
8 Second frame end face
9 Contact device
10 Counter-holding device
11 Counter-holding element
12 First frame axis
13 Second frame axis
14 Hinge area
15 Contact recess
16 Electrical contact
17 Slip-blocking surface
18 Cable interface
19 Cable
20 Conductor
21 Application surface
22 Spring element

What is claimed is:

1. A clamping device for electrically coupling a sensor cable to an electrical contact, the clamping device comprising:
   a circumferential, elastically deformable frame, the frame comprising a frame inner surface facing a frame inner area, a frame outer surface facing away from the frame inner area, a first frame end face and a second frame end face located opposite the first frame end face;
   a contact device connected to the frame and extending into the frame inner area;
   a counter-holding device arranged at the frame, the counter-holding device comprising a counter-holding element, wherein:
   the contact device and the counter-holding device are configured to form a receiving space for receiving as well as holding the electrical contact in a holding position of the clamping device;
   the clamping device is configured such that a relative movement of the counter-holding device in relation to the contact device into a first released position is brought about for releasing the electrical contact from the receiving space by a pressing on both sides against the frame outer surface on a first frame axis passing through the frame inner area; and
   the clamping device is configured such that a relative movement of the counter-holding device in relation to the contact device into a second released position different from the first released position is brought about for releasing the electrical contact from the receiving space by a pressing on both sides from the outside against the frame outer surface on a second frame axis passing through the frame inner area; and
   the second frame axis is different from the first frame axis.

2. A clamping device in accordance with claim 1, wherein the clamping device is configured such that the counter-holding device is caused to move away from the contact device by said pressing on both sides against the frame outer surface on the first frame axis.

3. A clamping device in accordance with claim 1, wherein the clamping device is configured such that the counter-holding element is caused to move away from the second frame axis by said pressing on both sides from the outside against the frame outer surface on the second frame axis.

4. A clamping device in accordance with claim 1, wherein:
   the counter-holding device further comprises another counter holding element to provide two counter-holding elements; and
   the clamping device is configured such that the counter-holding elements can be caused to move mutually away from one another by a pressing on both sides against the frame outer surface on the second frame axis.

5. A clamping device in accordance with claim 1, wherein:
   the frame further comprises a plurality of hinge areas; and
   the hinge areas are configured to yield in response to the pressing on both sides against the frame outer surface on the first frame axis and/or on the second frame axis.

6. A clamping device in accordance with claim 1, wherein the contact device comprises a contact recess for a partially enclosing contact of the electrical contact at a contact end facing the counter-holding device.

7. A clamping device in accordance with claim 1, wherein an electrical contact is arranged at the contact device for the electrical coupling of the clamping device to the electrical contact.

8. A clamping device in accordance with claim 7, wherein the electrical contact is configured such that an electrical coupling of the clamping device to the electrical contact is brought about both via the first frame end face and via the second frame end face of the clamping device.

9. A clamping device in accordance with claim 1, wherein the frame outer surface has at least partially a slip-blocking surface.

10. A clamping device in accordance with claim 1, wherein at least one of the frame end faces has a planar and/or arched configuration.

11. A clamping device in accordance with claim 1, further comprising a cable interface configured to electrically couple the clamping device to a cable, wherein the cable interface is configured for guiding the cable laterally in relation to the frame inner area.

12. A clamping device in accordance with claim 1, wherein the clamping device is formed of plastic in one piece.

13. A clamping device in accordance with claim 1, further comprising a spring element extrusion-coated with a plastic.

14. A sensor cable for the electrical coupling of an electrical contact with a diagnostic device, the sensor cable comprising:
an at least unipolar cable; and
a clamping device connected to the cable for the electrical coupling of the sensor cable to the electrical contact, the clamping device comprising:
a circumferential, elastically deformable frame, the frame comprising a frame inner surface facing a frame inner area, a frame outer surface facing away from the frame inner area, a first frame end face and a second frame end face located opposite the first frame end face;
a contact device connected to the frame and extending into the frame inner area;
a counter-holding device arranged at the frame, the counter-holding device comprising a counter-holding element, wherein:
the contact device and the counter-holding device are configured to form a receiving space for receiving as well as holding the electrical contact in a holding position of the clamping device;
the clamping device is configured such that a relative movement of the counter-holding device in relation to the contact device into a first released position is brought about for releasing the electrical contact from the receiving space by a pressing on both sides against the frame outer surface on a first frame axis passing through the frame inner area; and
the clamping device is configured such that a relative movement of the counter-holding device in relation to the contact device into a second released position different from the first released position is brought about for releasing the electrical contact from the receiving space by a pressing on both sides from the outside against the frame outer surface on a second frame axis passing through the frame inner area; and
the second frame axis is different from the first frame axis.

15. A sensor cable in accordance with claim 14, further comprising at least another clamping device to provide a plurality of clamping devices connected to the cable, wherein:
the cable comprises a multipolar configuration with a plurality of conductors; and
the plurality of clamping devices are each coupled electrically to a different one of the plurality of conductors of the cable.

16. A sensor cable in accordance with claim 14, wherein the at least one clamping device is cast integrally on the cable.

17. A sensor cable in accordance with claim 14, wherein the clamping device is configured such that the counter-holding device is caused to move away from the contact device by said pressing on both sides against the frame outer surface on the first frame axis.

18. A sensor cable in accordance with claim 14, wherein the clamping device is configured such that the counter-holding element is caused to move away from the second frame axis by said pressing on both sides from the outside against the frame outer surface on the second frame axis.

19. A sensor cable in accordance with claim 14, wherein:
the counter-holding device comprises another counter holding element to provide two counter-holding elements;
the clamping device is configured such that the counter-holding elements can be caused to move mutually away from one another by a pressing on both sides against the frame outer surface on the second frame axis.

20. A sensor cable in accordance with claim 14, wherein:
the frame further comprises a plurality of hinge areas; and
the hinge areas are configured to yield in response to the pressing on both sides against the frame outer surface on the first frame axis and/or on the second frame axis.

* * * * *